United States Patent [19]
Herrnstadt et al.

[11] Patent Number: 5,827,657
[45] Date of Patent: *Oct. 27, 1998

[54] DIRECT CLONING OF PCR AMPLIFIED NUCLEIC ACIDS

[75] Inventors: Corinna Herrnstadt, San Diego; Joseph M. Fernandez, Carlsbad, both of Calif.; Lloyd Smith; David A. Mead, both of Madison, Wis.

[73] Assignees: Invitrogen Corporation, San Diego, Calif.; Molecular Biology Resources, Inc., Milwaukee, Wis.

[*] Notice: The term of this patent shall not extend beyond the expiration date of Pat. No. 5,487,993.

[21] Appl. No.: 683,237

[22] Filed: Jul. 18, 1996

Related U.S. Application Data

[63] Continuation of Ser. No. 460,253, Jun. 2, 1995, abandoned, which is a continuation of Ser. No. 119,313, Sep. 9, 1993, Pat. No. 5,487,993, which is a continuation of Ser. No. 950,742, Sep. 24, 1992, abandoned, which is a continuation of Ser. No. 589,817, Sep. 27, 1990, abandoned.

[51] Int. Cl.$^6$ ..................................................... C12Q 1/68
[52] U.S. Cl. ............................................... 435/6; 536/23.1
[58] Field of Search ............................... 435/6, 91.2, 69.1

[56] References Cited

U.S. PATENT DOCUMENTS 4,965,188 10/1990 Mullis et al. .............................. 435/6

OTHER PUBLICATIONS

Clark, Nucleic Acids Research, 16(20):9677–978, 1988.

The 1988 Stratagene Catalog, p. 39.

Clark (1988) "Novel Non–Templated Nucleotide Addition Reactions Catalyzed by Procaryotic and Eucaryotic DNA Polymerases", *Nucl. Acids Res.* 16 (20) : 9677–9687.

Denney, et al. (1990) "DNA Generated by Polymerase Chain Reaction Using Taq DNA Polymerase has Non–Template Nucleotide Additions: Implications for Cloning PCR Products", *Amplification. A Forum for PCR Users*, No. 4, The Perkin Elmer Corporation US, pp. 25–26.

Hemsley, et al. (1989) "A Simple Method for Site–Directed Mutagenesis Using the Polymerase Chain Reaction", *Nucl. Acids Res.* 17 (16) :6545–6551.

Mole, et al. (1989) "Using the Polymerase Chain Reaction to Modify Expression Plasmids for Epitope Mapping", *Nucl. Acids Res.* 17 (8) :3319.

Morrow, et al. (1989) "Recombinant DNA Techniques" in Wu, *Methods in Enzymology* Academic Press, pp. 3–24.

Nelson, et al. (1979) "Addition of Homopolymers to the 3'–Ends of Duplex DNA with Terminal Transferase" in Wu, *Methods in Enzymology*, Academic Press, pp. 41–50.

New England Biolabs Catalog (1986/1987) p. 12.

New England Biolabs Catalog (1990/1991) pp. 91–95.

Roberts (1979) "Directory of Restriction Endonucleases" in Wu, *Methods in Enzymology*, Academic Press 68:27–41.

Stratagene Catalog (1988) pp. 56–57.

*Primary Examiner*—Scott W. Houtteman
*Attorney, Agent, or Firm*—Scully, Scott, Murphy & Presser

[57] ABSTRACT

Methods are described for producing recombinant DNA molecules from suitable host vectors and nucleic acids subjected to 3'-terminal transferase activity. In one embodiment, the method takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein. The invention also contemplates associated plasmid vectors and kits for implementing the methods.

6 Claims, 4 Drawing Sheets

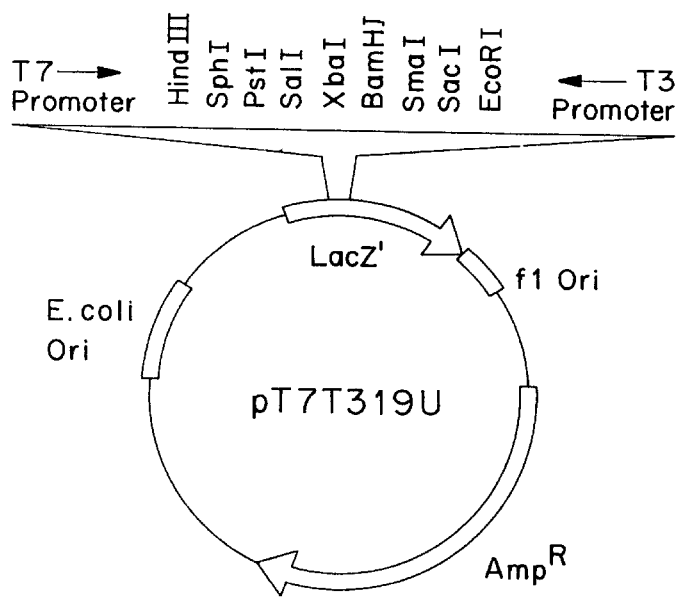
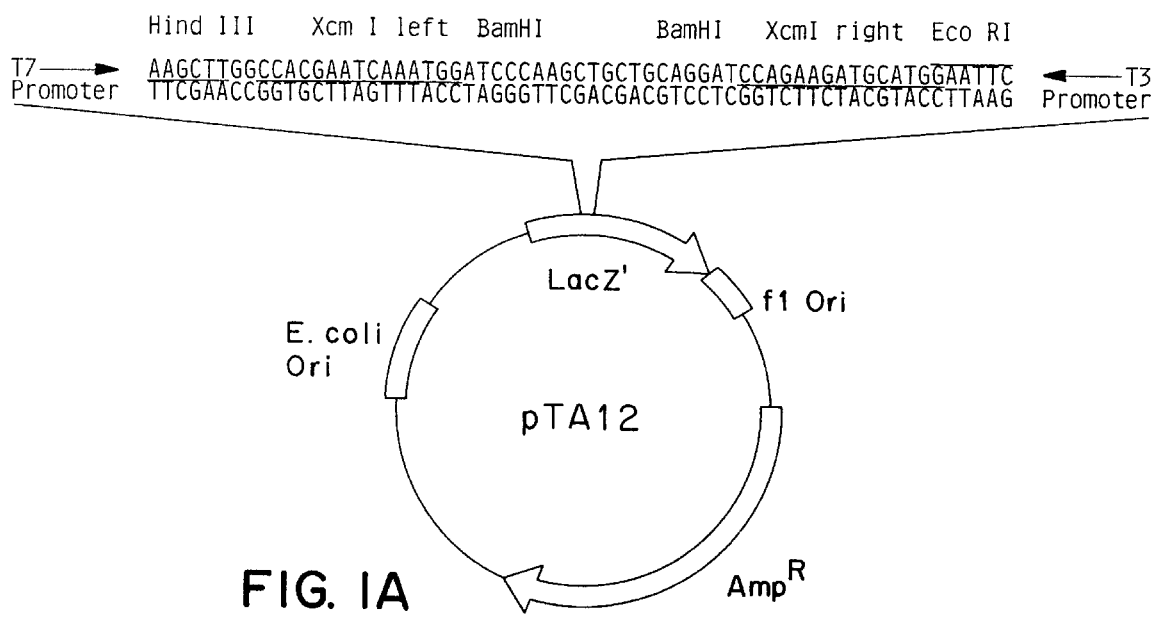
FIG. IA (a) underlined regions indicate restriction recognition sequences
(b) HphI digest, remove central fragment
(c) PCR amplified product (3'-dAMP) admixed; T4 DNA ligase.

DIRECT CLONING OF PCR AMPLIFIED NUCLEIC ACIDS

This application is a continuation of application Ser. No. 08/460,253, filed Jun. 2, 1995, now abandoned. which is a continuation of U.S. Ser. No. 08/119,313, filed Sep. 9, 1993, now U.S. Pat. No. 5,487,493; which is a continuation of U.S. application Ser. No. 07/950,742, filed Sep. 24, 1992, now abandon; which is a continuation of U.S. application Ser. No. 07/589,817, filed Sep. 27, 1990, now abandoned.

TECHNICAL FIELD

The present invention relates to the cloning of nucleic acids. More particularly, the invention relates to a simplified method for directly cloning polymerase generated nucleic acids into vectors.

BACKGROUND

In the short time that practical PCR techniques for amplifying nucleic acid material have been available, many applications have been advanced. For example, PCR has found numerous research applications, such as in the determination of genetic mutations, in engineering template-modified sequences using mismatched primer sequences, and in producing sufficient genetic material for direct sequencing. PCR has also been applied to many medical and legal problems where it has been used in such areas as diagnosis of monogenic diseases, analysis of biological evidence, etc. Further applications of PCR amplification are discussed in a number of references. See, e.g., *PCR Technology*, H. A. Erlich, ed., Stockman Press, 1989. Doubtless, many more applications will be forthcoming.

In PCR, specific nucleic acid target sequences are transcribed by a chain reaction in which a primer molecule complementary to a particular section of a nucleic acid template is used to form an extension product of the primer. Each primer extension product specifically anneals with a complementary primer molecule and the resulting primed template acts as a substrate for a further extension reaction. These steps are repeated many times, preferably using an automated cycling procedure, thereby exponentially amplifying the initial nucleic acid material. PCR is particularly useful in detecting nucleic acid sequences that are initially present in only very small amounts. Procedures for conducting PCR have been extensively described. See, for example, U.S. Pat. Nos. 4,683,195 and 4,683,202, both to Mullis, et al., which descriptions are incorporated herein by reference.

Modernly, PCR is performed by automated cycling of denaturation, oligonucleotide primer annealing to a genetic template, and primer extension using a thermostable DNA polymerase, e.g., the Taq enzyme isolated from the bacterium *Thermus Aquaticus*. See, e.g., U.S. Pat. No. 4,889,818 issued to Gelfand et al, which description is incorporated herein by reference.

While PCR alone may be satisfactory for certain applications, e.g., direct sequencing, often it is desirable to obtain a clone of PCR amplified products for further analysis, modification, or synthesis of probes. For example, a number of mRNA species exhibit polymorphic transcripts. Alternative splicing of the mRNA species to give multiple transcripts can be unambiguously sequenced after molecular cloning of the PCR amplification products (Frohman et al., Proc. Natl. Acad. Sci. USA 85: 8998–9002 (1988)). Cloning of PCR generated samples to construct cDNA libraries may also be desired. Generally, a protocol entailing cloning of PCR products can be expected tG generate a smaller set of products than PCR alone, thereby reducing the background associated with direct sequencing of PCR products.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation. Thus, typical PCR cloning methods require preparation of PCR primer molecules attached to "add on" base sequences having a preferred restriction recognition sequence. Also, these methods can result in unintended internal restriction of uncharacterized or polymorphic sequences. Such limitations of previous methods add to the cost and complexity of cloning PCR products routinely.

Recently, it was reported that Taq polymerase catalyzes the nontemplated addition of single deoxyadenosine monophosphate (dAMP) residues to the 3' termini of blunt-ended DNA duplexes (Clark, J. M., Nucl. Acids Res. 20:9677–86 (1989)). Thus, Taq polymerase (and other thermostable polymerases) naturally creates restriction-like termini on DNA fragments. However, since these overhanging residues are widely viewed as incompatible with most molecular cloning schemes, the residues are routinely removed with nucleases to create blunt ends, such as S1, Klenow, and T4.

In view of the above considerations, a method is desired for directly cloning PCR products containing terminal 3'-dAMP residues into appropriate plasmids. Such method would eliminate the need for preparing primers having restriction recognition sequences and it would eliminate the need for a restriction step to prepare the PCR product for cloning. Additionally, such method would preferably allow cloning PCR products directly without an intervening purification step.

BRIEF SUMMARY OF THE INVENTION

The present invention is for a method of 5 producing recombinant DNA nucleic acid molecules that include a DNA segment having terminal 3'-dAMP residues. Such DNA segments are generated by thermophilic polymerases during PCR amplification.

Thus, in one embodiment of the invention, the method involves subjecting a target DNA segment to PCR amplification so that a plurality of double-stranded nucleic acids including the segment are formed with each double stranded nucleic acid having a single overhanging 3'- deoxyadenosine monophosphate (dAMP) residue. The double-stranded nucleic acids are admixed with a heterologous source of linear double-stranded DNA molecules, such as linearized plasmids, which are provided with a single overhanging deoxythymidylate (dTMP) residue at the 3' termini of the DNA molecules. The reaction mixture is maintained under predetermined ligation conditions to effect ligation of the 3'-dAMP-containing nucleic acids with the 3'-dTMP-containing DNA molecules to give the recombinant molecules.

In a preferred embodiment of the invention the target DNA segment will be a gene. In further preferred embodiments of the invention a suitable host cell line will be transformed with the gene and the gene will be maintained under predetermined reaction conditions which allow expression of the gene.

The present invention affords plasmids that comprise a first nucleotide sequence recognized by a restriction enzyme and a second nucleotide sequence recognized by a second restriction enzyme. Each recognition sequence is capable of generating a single terminal 3'-dTMP group upon reaction with the restricton enzymes. In a further preferred embodiment of the invention the restriction enzymes will be identical and either Xcm 1 or Hph 1. In further preferred embodiment, the DNA fragment that is removable upon restriction is synthesized as an oligonucleotide with additional restriction sites flanking the first set of restriction sites so that the oligonucleotide may be inserted readily into a suitable substrate.

Kits suitable for directly cloning PCR amplification products having 3'-dAMP residues into the instant plasmids are afforded by the present invention. The kits will include plasmids having at least two nucleotide sequences recognized by a restriction enzyme capable of generating single 3'-dTMP termini at each sequence. The kits will also include a restriction enzyme capable of cleaving the plasmids at each nucleotide sequence. Also, the kits may include DNA ligase capable of ligating the heterologous strands of PCR amplified DNA with the plasmids at the restriction sites.

The present invention thus affords novel methods and associated plasmids and kits for directly cloning recombinant DNA molecules from polynucleotides that have terminal 3'-deoxyAMP residues, such as those produced by PCR amplification. Amplified nucleic acids from genomic DNA, cDNA, or recombinant vectors, having DNA inserts, such as lambda phages, cosmids and YACS may be used. The instant cloning methods allow the generation of large amounts of genetic material via cell transformation, thereby making the direct sequencing of long nucleotide sequences feasible. Sequence information obtained by the present invention will be more reliable than previously available from direct sequencing of PCR amplification products due to more specific ligation reactions and reduced numbers of restriction fragments. Such methods will be particularly useful in cDNA cloning efforts. The instant methods will also afford improved templates for synthesizing probes useful in genetic mapping and cloning projects, as well as hard copies of critical diagnostic samples, e.g., as in genetic fingerprinting. Also, the present invention affords reduced cost and simplicity to current PCR protocols due to elimination of the need for synthesizing primer sequences with specific recognition sequences, as well as the need for associated restriction steps.

BRIEF DESCRIPTION OF THE DRAWINGS

FIG. 1A depicts an exemplary cloning vector constructed according to the principles or the present invention. The genetic maps of host vector (pT7T319U) and cloned vector (pTA12) are shown.

DETAILED DESCRIPTION OF THE INVENTION

A. Definitions

Figure 1B:
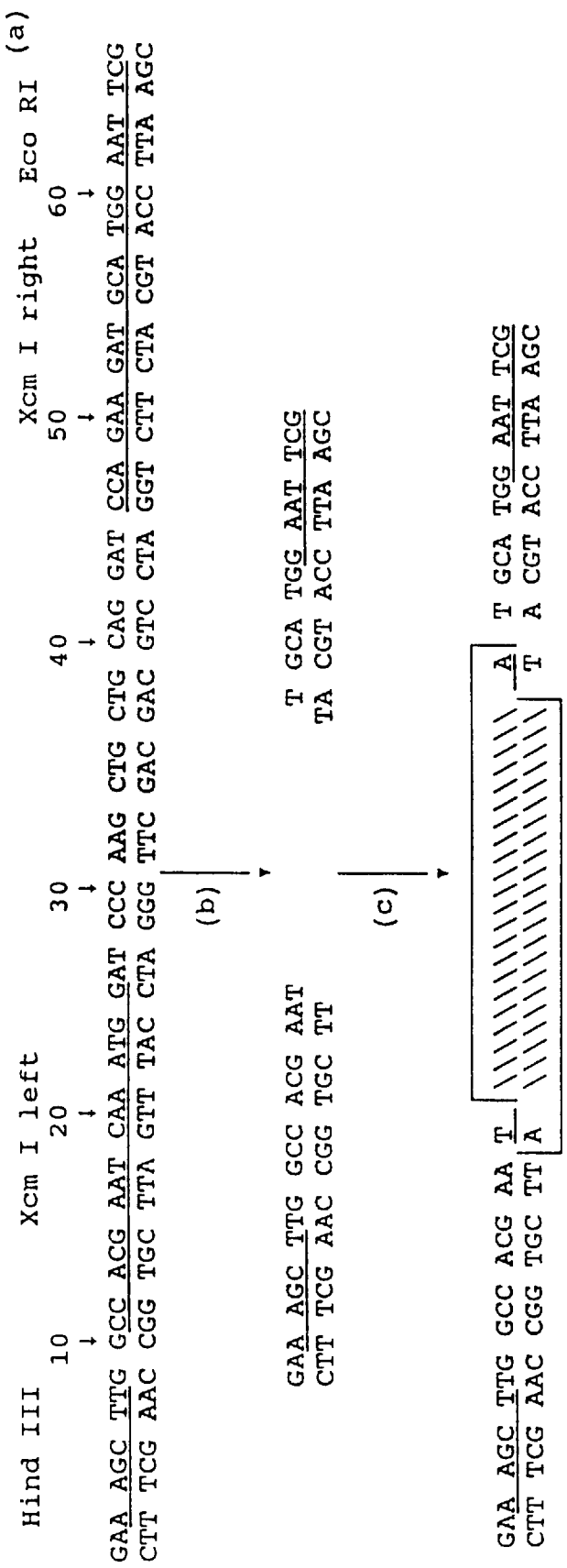
FIG. 1B presents a representative DNA sequence of plasmids constructed according to the principles of the present invention. The plasmids are provided with two Xcm 1 restriction sites between Hind III and Eco RI sites. Also the result of Xcm 1 digestion is shown as well as the result of ligation with a 3'-dAMP PCR amplified product.

Base Pair (bp): a partnership of adenine (A) with thymine (T), or of cytosine (C) with guanine (G) in a double stranded DNA molecule. In RNA, uracil (U) is substituted for thymine. Base pairs are said to be "complementary" when their component bases pair up normally when a DNA or RNA molecule adopts a double stranded configuration.

Complementary Nucleotide Sequence: a sequence of nucleotides in a single-stranded molecule of DNA or RNA that is sufficiently complementary to another single strand to specifically (non-randomly) hybridize to it with consequent hydrogen bonding.

Conserved: a nucleotide sequence is conserved with respect to a preselected (reference) sequence if it non-randomly hybridizes to an exact complement of the preselected sequence.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA—DNA duplex comprising two DNA strands (ds DNA), or an RNA-DNA duplex comprising one DNA and one RNA strand.

Gene: a nucleic acid whose nucleotide sequence codes for a RNA, DNA or polypeptide molecule. Genes may uninterrupted sequences of nucleotides or they may include such intervening segments as introns, promoter regions, splicing sites and repetitive sequences. A gene can be either RNA or DNA.

Hybridization: the pairing of complementary nucleotide sequences (strands of nucleic acid) to form a duplex, heteroduplex, or complex containing more than two single-stranded nucleic acids, by establishing hydrogen bonds between/among complementary base pairs. Hybridization is a specific, i.e. non-random, interaction between/among complementary polynucleotides that can be competitively inhibited.

Hybridization product: the product (also called a "hybrid" or "duplex") formed when a polynucleotide hybridizes to a single or double-stranded nucleic acid. When a polynucleotide hybridizes to a double-stranded nucleic acid, the hybridization product formed is referred to as a triple helix or triple-stranded nucleic acid molecule. Moser et al, *Science*, 238:645–50 (1987).

Nucleotide: a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Nucleotide Analoa: a purine or pyrimidine nucleotide that differs structurally from an A, T, G, C, or U base, but is sufficiently similar to substitute for the normal nucleotide in a nucleic acid molecule. Inosine (I) is a nucleotide analog that can hydrogen bond with any of the other nucleotides, A, T, G, C, or U. In addition, methylated bases are known that can participate in nucleic acid hybridization.

Polvnucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides (relatively short polynucleotides), genes, vectors, plasmids, and the like.

Primer: a polynucleotide, whether purified from a nucleic acid restriction digest or produced synthetically, that is capable of acting as a point of initiation of synthesis when placed under conditions in which synthesis of a primer extension product complementary to a template nucleic acid strand is induced, i.e., in the presence of nucleotides and an agent for polymerization, such as DNA polymerase, reverse transcriptase and the like, under suitable temperature and pH reaction conditions.

Recombinant DNA (rDNA) molecule: a DNA molecule produced by operatively linking a nucleic acid sequence, such as a gene, to a DNA mole[]ule sequence of the present invention. Thus, a recombinant DNA molecule is a hybrid DNA molecule comprising at least two nucleotide sequences not normally found together in Nature. rDNA's not having a common biological origin, i.e., evolutionarily different, are said to be "heterologous".

Vector: a DNA molecule capable of autonomous replication in a cell and to which a DNA segment, e.g., gene or polynucleotide, can be operatively linked so as to bring about replication of the attached segment. Vectors capable of directing the expression of genes encoding for one or more proteins are referred to herein as "expression vectors". Particularly important vectors allow cloning of cDNA (complementary DNA) from mRNAs produced using reverse transcriptase.

B. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way. A DNA target sequence of the present invention comprises no more than about 2000 nucleotide base pairs and may include a structural gene. Usually, the DNA sequence is present as an uninterrupted linear series of codons where each codon codes for an amino acid residue, i.e., the DNA sequence contains no introns.

However, the invention also contemplates any desired target fragment, such as a nucleic acid having an intervening sequence, a promoter, a regulatory sequence, a repetitive sequence, a flanking sequence, or a synthetic nucleic acid.

A DNA segment of the present invention can easily be synthesized by chemical techniques, for example, via the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence.

The DNA segments of the present invention typically are duplex DNA molecules having cohesive termini, i.e., "overhanging" single-stranded portions that extend beyond the double-stranded portion of the molecule. The presence of cohesive termini on the DNA molecules of the present invention is generally preferred.

Also contemplated by the present invention are ribonucleic acid (RNA) equivalents of the above described DNA segments.

C. PCR Primers

The present invention contemplates using the PCR technique described hereinbelow, to generate enhanced amounts of a target nucleotide sequence. The PCR technique employs primer molecules to initiate the primer elongation reaction. The primer must be sufficiently long to prime the synthesis of extension products in the presence of the agents for polymerization. The exact lengths of the primers will depend on many factors, including temperature and the source of primer. For example, depending on the complexity of the template sequence, a polynucleotide primer typically contains 15 to 25 or more nucleotides, although it can contain fewer nucleotides. As few as 8 nucleotides in a polynucleotide primer have been reported as effective for use. Studier et al, *Proc. Natl. Acad. Sci. USA*, 86:6917–21 (1989). Short primer molecules generally require lower temperatures to form sufficiently stable hybridization complexes with template to initiate primer extension.

The primers used herein are selected to be "substantially" complementary to the different strands of each specific sequence to be synthesized or amplified. Accordingly, the primer must contain at its 3' terminus a nucleotide sequence sufficiently complementary to nonrandomly hybridize with its respective template strand. Therefore, the primer sequence may not reflect the exact sequence of the template. For example, a non-complementary polynucleotide can be attached to the 5' end of the primer, with the remainder of the primer sequence being substantially complementary to the strand. Such noncomplementary polynucleotides might code for a site for protein binding or simply be used to adjust the reading frame of the codons. Alternatively, noncomplementary bases or longer sequences can be interspersed into the primer, provided the primer sequence has sufficient complementarity with the sequence of the template strand to allow non-random hybridization to occur so that an extension product can be formed under polynucleotide synthesizing conditions.

Sommer, et al., *Nuc. Acid Res.*, 17:6749 (1989), reports that primers having as little as a 3 nucleotide exact match at the 3' end of the primer is capable of specifically initiating primer extension products, although less nonspecific hybridization occurs when the primer contains more nucleotides at the 3' end having exact complementarity with the template sequence. Therefore, a substantially complementary primer as used herein must contain at its 3' end at least 3 nucleotides having exact complementarity to the template sequence. A substantially complementary primer preferably contains at least 10 nucleotides, more preferably at least 18 nucleotides, and still more preferably at least 24 nucleotides, at its 3' end having the aforementioned complementarity. Still more preferred are primers whose entire nucleotide sequence have exact complementarity with the template sequence.

The choice of a primer's nucleotide sequence depends on factors such as the distance on the nucleic acid from the region coding for the desired specific nucleic acid sequence present in a nucleic acid of interest and its hybridization site on the nucleic acid relative to any second primer to be used.

The primer is preferably provided in single-stranded form for maximum efficiency, but may alternatively be double-stranded. If double-stranded, the primer is first treated to separate its strands before being used to prepare extension products. Preferably, the primer is a polydeoxyribonucleotide.

Polynucleotides can be prepared by a variety of methods Including de novo chemical synthesis and derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a polynucleotide can be conducted using any suitable method, such as, for example, the phosphotriester or phosphodiester methods. See Narang et al, *Meth. Enzymol.*, 68:90, (1979); U.S. Pat. No. 4,356,270; Itakura et al, *Ann. Rev. Biochem.*, 53:323–56 (1989); and Brown et al, *Meth. Enzymol.*, 68:109, (1979).

Derivation of a polynucleotide from nucleic acids involves the cloning of a nucleic acid into an appropriate host by means of a cloning vector, replication of the vector and therefore multiplication of the amount of the cloned nucleic acid, and then the isolation of subfragments of the cloned nucleic acids. For a description of subcloning nucleic acid fragments, see Maniatis et al, *Molecular Clonina: A Laboratory Manual*, Cold Spring Harbor Laboratory, pp 390–401 (1982); and see U.S. Pat. Nos. 4,416,988 and No. 4,403,036.

D. Hybridization

Template nucleic acid sequences to be hybridized in the present methods can be present in any nucleic acid-containing sample so long as the sample is in a form, with respect to purity and concentration, compatible with nucleic acid hybridization reaction. Isolation of nucleic acids to a degree suitable for hybridization is generally known and can be accomplished by a variety of means. For instance, nucleic acids can be isolated from a variety of nucleic acid-containing samples including body tissue, such as skin, muscle, hair, and the like, and body fluids such as blood, plasma, urine, amniotic fluids, cerebral spinal fluids, and the like. See, for example, Maniatis et al, *Molecular Cloning: A Laboratory Manual*, Cold Spring Harbor Laboratory (1982); and Ausubel et al, *Current Protocols in Molecules Biology*, John Wiley and Sons (1987).

The hybridization reaction mixture is maintained under hybridizing conditions for a time period sufficient for the primer to hybridize to complementary nucleic acid sequences present in the sample to form a hybridization product, i.e., a complex containing primer and template nucleic acid strands.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the primer to anneal with the template sequence, typically to form a nucleic acid duplex. Such time, temperature and pH conditions required to accomplish hybridization depend, as is well known in the art, on the length of the primer to be hybridized, the degree of complementarity between the primer and the template, the guanosine and cytidine content of the polynucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 18° C. to 75° C., preferably about 37° C. to about 65° C., more preferably about 54° C., and for time periods from 0.5 seconds to 24 hours, preferably 2 min.

Hybridization can be carried out in a homogeneous or heterogeneous format as is well known. The homogeneous hybridization reaction occurs entirely in solution, in which both the primer and template sequences to be hybridized are present in soluble forms in solution. A heterogeneous reaction involves the use of a matrix that is insoluble in the reaction medium to which either the primer or template is bound.

Also preferred are the homogeneous hybridization reactions such as are conducted for a reverse transcription of isolated mRNA or viral RNA to form cDNA, dideoxy sequencing and other procedures using primer extension reactions in which primer hybridization is a first step. Particularly preferred is the homogeneous hybridization reaction in which the template is amplified via a polymerase chain reaction (PCR).

Where the nucleic acid containing a template sequence is in a double-stranded (ds) form, it is preferred to first denature the dsDNA, as by heating or alkali treatment, prior to conducting the hybridization reaction. The denaturation of the dsDNA can be carried out prior to admixture with a primer to be hybridized, or it can be carried out after the admixture of the dsDNA with the primer. Where the primer itself is provided as a double-stranded molecule, it too can be denatured prior to admixture, or it can be denatured concurrently with the template-containing dsDNA.

E. Primer Extension Reactions

The primed template can be used to produce a strand of nucleic acid having a nucleotide sequence complementary to the template, i.e., a template-complement.

If the template whose complement is to be produced is in the form of double stranded nucleic acid, it is typically first denatured, usually by melting, into single strands, such as ssDNA. The nucleic acid is then subjected to a (first) primer extension reaction by treating (contacting) the nucleic acid with a (first) polynucleotide synthesis primer having as a portion of its nucleotide sequence a sequence selected to be substantially complementary to a portion of the sequence of the template. The primer is capable of initiating a primer extension reaction by hybridizing to a specific nucleotide sequence, preferably at least about 8 nucleotides in length and more preferably at least about 20 nucleotides in length. This is accomplished by mixing an effective amount of the primer with the template nucleic acid, and an effective amount of nucleotide reactants to form a primer extension reaction admixture. The admixture is maintained under polynucleotide synthesizing conditions for a time period, which is typically predetermined, sufficient for the formation of a primer extension reaction product.

The primer extension reaction is performed using any suitable method. Generally polynucleotide synthesizing conditions are those wherein the reaction occurs in a buffered aqueous solution, preferably at a pH of 7-9, most preferably about 8. Preferably, a molar excess (for genomic nucleic acid, usually about $10^6:1$ primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 ug, preferably 250 ng, of primer per 100 ng to 500 ng of mammalian genomic DNA or per 10 to 50 ng of plasmid DNA.

The deoxyribonucleotide triphosphates (dNTPs) dATP, dCTP, dGTP, and dTTP are also admixed to the primer extension reaction admixture in amounts adequate to support the synthesis of primer extension products, and depends on the size and number of products to be synthesized. The resulting solution is heated to about 90° C.–100° C. for about 1 to 10 minutes, preferably from 1 to 4 minutes. After this heating period the solution is allowed to cool to room temperature, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. Thus, for example, if DNA polymerase is used as inducing agent, the temperature is generally no greater than about 40° C. unless the polymerase is heat-stable.

The inducing agent may be any compound or system which will function to accomplish the synthesis of primer extension products, including enzymes.

Suitable enzymes for this purpose include, for example, *E. coli* DNA polymerase I, Klenow fragment of *E. coli* DNA polymerase I, T4 DNA polymerase, T7 DNA polymerase, recombinant modified T7 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand.

Heat-stable (thermophilic) DNA polymerases are particularly preferred as they are stable in a most preferred embodiment in which PCR is conducted in a single solution in which the temperature is cycled. Representative heat-stable polymerases are the DNA polymerases isolated from *Bacillus stearothermophilus* (Bio-Rad, Richmond, Calif.), *Thermus thermophilus* (FINZYME, ATCC #27634), *Thermus species* (ATCC #31674), *Thermus aquaticus* strain TV 1151B (ATCC #25105), *Sulfolobus acidocaldarius*, described by Bukhrashuili et al, *Biochem. Biophys. Acta*, 1008: 102–7 (1989) and by Elie et al, *Biochem. Biophys. Actz*, 951:261–7 (1988), *Thermus filiformis*. (ATCC #43280), the polymerase isolated from *Thermus flavus* (Molecular Biology Resources; Milwaukee, Wis.), and "Vent" polymerases (New England Biolabs, Beverly, Mass.).

Particularly preferred is Taq DNA polymerase available from a variety of sources including Perkin Elmer Cetus, (Norwalk, Conn.), Promega (Madison, Wis.) and Stratagene (La Jolla, Calif.), and AmpliTaq™ DNA polymerase, a recombinant Taq DNA polymerase available from Perkin-Elmer Cetus.

In a preferred embodiment the polymerase selected will serve as a 40-terminal transferase that is capable of placing a single, overhanging nucleotide residue on a double-stranded nucleic acid. In a most preferred embodiment the transferase will attach a 3'-adenosine residue to an untemplated nucleic acid, such as performed by Taq polymerase. In alternative embodiments, the transferase will add other nucleosides, e.g., guanosine, cytidine, thymidine.

This invention contemplates any nucleic acid segment produced by a polymerase either in vitro or in vivo. Any polymerase capable of producing a double-stranded nucleic acid having a protruding 3' terminal AMP facilitating its insertion into a vector of the present invention is useful in practicing the invention. Particularly preferred are DNA dependent DNA polymerases and RNA dependent DNA polymerases. DNA dependent DNA polymerases include the TAQ polymerase.

Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The primer extension reaction product can then be subjected to a second primer extension reaction by treating it with a second polynucleotide synthesis primer having a preselected nucleotide sequence. The second primer is capable of initiating the second reaction by hybridizing to a nucleotide sequence, preferably at least about 8 nucleotides in length and more preferably at least about 20 nucleotides in length, found in the first product. This is accomplished by mixing the second primer, preferably a predetermined amount thereof, with the first product, preferably a predetermined amount thereof, to form a second primer extension reaction admixture. The admixture is maintained under polynucleotide synthesizing conditions for a time period, which is typically predetermined, sufficient for the formation of a second primer extension reaction product.

In preferred strategies, the first and second primer extension reactions are the first and second primer extension reactions in a polymerase chain reaction (PCR).

PCR is carried out by cycling, i.e., sequentially performing in one admixture, the above described first and second primer extension reactions, each cycle comprising polynucleotide synthesis followed by denaturation of the double stranded polynucleotides formed. Methods and systems for amplifying a specific nucleic acid sequence are described in U.S. Pat. No. 4,683,195 and No. 4,683,202, both to Mullis et al; and the teachings in *PCR Technology*, Erlich, ed., Stockton Press (1989); Falcona et al, *Methods in Enzvmol.*, 155:335–50 (1987); and *Polymerase Chain Reaction*, Erlich et al, eds., Cold Spring Harbor Laboratories Press (1989).

F. PCR Cycling

PCR is carried out by cycling the following steps on one admixture: 1) denaturing step to form single-stranded templates, 2) hybridization step to hybridize primer to ss template, and 3) primer extension steps to form the extended product. PCR is performed in the above sequence (cycle) by changing the temperature of the PCR mixture to a temperature compatible with each step, in series.

The primer extension reaction conditions involve maintaining the reaction mixture for a time period and at a temperature sufficient for a DNA polymerase primer extension reaction to occur to produce primer extension products as is well known. Conditions for conducting a primer extension reaction are well known. In a PCR format, the maintenance is carried out quickly to conveniently facilitate numerous cycles, in about 1 second to 5 minutes, preferably about 1.5 minutes, and at about 40° C. to 75° C., preferably about 72° C. Conducting at least one cycle of PCR results in the formation of amplified nucleic acid products. The PCR is typically conducted with at least 15 cycles, and preferably with about 20 to 40 cycles.

Hybridizing conditions were described earlier and are suitable for use in the PCR format. However, it is preferred and convenient to conduct hybridization in short periods of time, in 5 seconds to 12 minutes, preferably in 2 minutes, and in the temperature range of 30° C. to 75° C., preferably about 40° C. to 65° C., and more preferably about 54° C.

G. Detection of PCR product

Detection of amplified nucleic acid product can be accomplished by any of a variety of well known techniques. In a preferred embodiment, the amplified product is separated on the basis of molecular weight by gel electrophoresis, and the separated products are then visualized by the use of nucleic acid specific stains which allow one to observe the discrete species of resolved amplified product present in the gel. Although numerous nucleic acid specific stains exist and would be suitable to visualize the electrophoretically separated nucleic acids, ethidium bromide is preferred.

Alternative methods suitable to detect the amplified nucleic acid product include hybridization-based detection means that use a labeled polynucleotide probe capable of hybridizing to the amplified product. Exemplary of such detection means include the Southern blot analysis, ribonuclease protection analysis using in vitro labeled polyribonucleotide probes, and similar methods for detecting nucleic acids having specific nucleotide sequences. See, for example, Ausubel et al., *Current Protocols in Molecular Biology*, John Wiley & Sons, 1987.

In one approach for detecting the presence of a specific nucleic acid sequence, the deoxyribonucleotide triphosphates (dNTPs) used in the primer extension reaction include a label or indicating group that will render a primer extension product detectable. Typically such labels include radioactive atoms, chemically modified nucleotide bases, and the like.

Radioactive elements operatively linked to or present as part of a dNTP provide a useful means to facilitate the detection of a DNA primer extension product. A typical radioactive element is one that produces beta ray emissions. Elements that emit beta rays, such as $^3H$, $^{14}C$, $^{32}P$, and $^{35}S$ represent a class of beta ray emission-producing radioactive element labels.

Alternatives to radioactively labeled dNTPs are dNTPs that are chemically modified to contain metal complexing agents, biotin-containing groups, fluorescent compounds, and the like.

One useful metal complexing agent is a lanthanide chelate compound formed by a lanthanide metal and beta-diketonate ligands, the lanthanide being bound to the nucleic acid or polynucleotide via a chelate forming compound such as an EDTA-analogue so that a fluorescent lanthanide complex is formed. See U.S. Pat. No. 4,374,120, and No. 4,569,790 and published International Patent Applications No. EP0139675 and No. WO87/02708.

Biotin or acridine ester-labeled oligonucleotides and their use in polynucleotides have been described. See U.S. Pat. No. 4,707,404, published International Patent Application EP0212951 and European Patent No. 0087636. Useful fluorescent marker compounds include fluorescein, rhodamine, Texas Red, NBD and the like.

A labeled nucleotide residue present in a nucleic acid renders the nucleic acid itself labeled and therefore distinguishable over other nucleic acids present in a sample to be assayed. Detecting the presence of the label in the nucleic acid and thereby the presence of the specific nucleic acid sequence, typically involves separating the nucleic acid from any labeled dNTP that is not present as part of a primer extension reaction product.

Techniques for the separation of single stranded polynucleotide, such as non-hybridized labeled polynucleotide probe, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is $^{32}P$. Southern, *J. Mol. Biol.*, 98:503 (1975).

In another approach for detecting the presence of a DNA duplex, and the one used herein as exemplary of a preferred embodiment, the DNA duplex is amplified as described herein and the resulting amplified nucleic acid product is detected.

Numerous applications of the PCR-based amplification method are contemplated that will be readily apparent to one skilled in the art. For example, cloning mRNA through reverse transcription to produce cDNA can be made more sensitive by the use of PCR-based amplification of the produced cDNA. Insofar as nucleic acid sequencing can be conducted on PCR-amplified nucleic acid, the present invention can be used to improve sequencing of amplified nucleic acids.

H. Recombinant DNA Molecules

As is well known in the art, the choice of vector to which a DNA target sequence of the present invention is operatively linked depends upon the functional properties desired, e.g., protein expression, and upon the host cell to be transformed. These limitations are inherent in the art of constructing recombinant DNA molecules. However, a vector contemplated by the present invention is at least capable of directing the replication, and preferably also expression, of a gene operatively linked to the vector.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon may also include a gene whose expression confers drug resistance to a bacterial host transformed therewith. Typical bacterial drug resistance genes are those that confer resistance to ampicillin, tetracycline, or kanamycin.

Those vectors that include a procaryotic replicon can also include a procaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a PCR product molecule of the present invention. Typical of such vector plasmids are pUC8, pUC9, pBR322 and pBR329 available from Bio-Rad Laboratories, (Richmond, Calif.) and pPL, pKK223, pTZ18U, pTZ19U, and pT7T319U, available from Pharmacia, (Piscataway, N.J.).

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired gene. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in a eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730–37 (1984).

In a preferred embodiment of the present invention, the selected vector in its linearized form will have cohesive termini-complementary to the termini generated by the polymerase, e.g., Taq polymerase, used in PCR amplification. Thus, a suitable vector preparation for directly cloning 3'-dAMP-terminal PCR products will be a plasmid having single, overhanging 3'-dTMP termini in its linearized form. (The dTMP moiety may have its monophosphate group attached to the 3' or, more preferably, to the 5' end of the thymidine nucleoside.)

Since thymine is not complementary with itself, the 3'-dTMP terminal vectors used will be derived from larger plasmids which include a removable linking fragment that joins the two 3'-dTMP groups until it is desired to form the linearized vector. The linearized vector will be generated from the larger plasmid by restriction at the desired dTMP sites using the restriction enzymes described herein according to procedures well-known in the art and available from the appropriate enzyme supplier.

The present invention may be used to insert a cDNA fragment into a vector of the present invention. Preferably, the cDNA is inserted into the vector in a directional manner. This can be accomplished by employing a primer polynucleotide containing a cleavage site such as a restriction endonuclease site to allow the protruding 3' AMP to be cleaved off of one end of the cDNA. This restriction endonuclease site is used to insert this restriction endonuclease-cleaved end of the cDNA into the vector. The other end of the cDNA is inserted into the vector using the protruding 3' AMP present on that end of the cDNA to facilitate insertion into a vector of the present invention having a protruding 5' TMP. This procedure allows the cDNA to be inserted into a vector in a directional manner facilitating the expression of the DNA cloned.

In preferred embodiments, the primer containing the cleavage site employed to insert a cDNA into a vector of the present invention is a polymerase chain reaction primer. Preferably, the second primer employed in the polymerase chain reaction does not contain the cleavage site. A vector of the present invention may be an expression vector, a cloning vector, a shuttle vector, and the like.

A most preferred embodiment of the invention will entail using a restriction enzyme capable of generating single, overhanging 3'-dTMP termini. However, only a few restriction enzymes are known that can be specified to generate such termini in plasmids, i.e., Hph 1, Mbo II, and Xcm I (New England Biolabs). Moreover, two of these enzymes (Mbo II and Xcm I) show low ligation efficiencies (<20%). Also, two enzymes (Hph I and Mbo II) apparently find recognition sequences in virtually every known plasmid, e.g., each restricts the pUC19 plasmid at 7 sites, thereby producing many undesired fragments. Therefore, it may be desirable to screen the above enzymes for their activities and ligation efficiencies in particular applications. These methods are well known to those skilled in the art and are illustrated by the examples described hereinbelow.

A variety of methods have been developed to operatively link DNA to vectors via complementary cohesive termini. For instance, complementary homo or heteropolymeric tracts can be added to the ends of the dAMP-terminal linking fragments that are removable from the vector with a restriction enzyme when it is desired to ligate the 3'-dAMP terminal products generated by PCR. Thus, the vector is covalently joined to the removable fragment via linking sequences and by hydrogen bonding between the complementary tails of the vector and linking sequence and between the linking sequences and removable fragment.

In a most preferred embodiment, the plasmid selected as vector will have Eco RI and Hind III restriction sites that allow insertion of a DNA sequence having at its termini complementary residues that allow restriction with Eco RI and Hind III. The internal region of the fragment will have two or more restriction sites recognized by the enzymes Xcm I, Hph I, or Mbo II, or a combination thereof, so that 3'-terminal dTMP residues can be generated for subsequent joining to 3'-dAMP terminal DNA segments. Restriction of the appropriate recognition sequences produces a removable DNA fragment and linearized plasmid. The smaller DNA Fragment can be removed by gel separation techniques well-known to those in the art.

Synthetic linkers containing a variety of restriction sites are commercially available from a number of sources including International Biotechnologies, Inc., New Haven, Conn. Instructions for their use can be obtained from the supplier. Polynucleotide sequences, including the removable fragments and/or the linking sequences are preferably prepared by direct synthesis techniques such as those described for making PCR primer molecules.

Also contemplated by the present invention are RNA equivalents of the above described recombinant DNA molecules.

The 3'-dAMP nucleic acids are combined with linear DNA molecules in an admixture thereof and a ligase will be added to effect ligation of the components. Any ligase available commercially is contemplated to perform the ligation reaction effectively using methods and conditions well known to those skilled in the art. A preferred ligase is T4 DNA ligase.

Volume exclusion agents may also be used to accelerate the ligation reaction. However, such agents may cause excessive intramolecular circularizations in some cases.

Notably, it is also contemplated that certain nucleic acids desired to be cloned will have only one terminal 3'-dAMP residue per duplex. This situation may arise from incomplete reaction of a PCR polymerase, e.g., Tag, with amplified product. However, the present invention anticipates such eventuality, and will allow in some cases direct cloning of monoligated (linear) recombinants as long as the nucleic acid desired to be cloned binds to at least one terminal 3'-dTMP residue presented by the vector. Additionally, transformation of cells with monoligated recombinant DNA molecules will likely occur normally in these cases with ligation at the second 3'-dTMP terminus occurring intracellularly.

I. Transformation of Cells

The present invention also relates to introducing the recombinant DNA molecules of the present invention into host cells, via a procedure commonly known as transformation or transfection. The host cell can be either procaryotic or eucaryotic. Bacterial cells are preferred procaryotic host cells and typically are a strain of *E. coli* such as, for example, the DH1αF strain. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. One preferred means of effecting transformation is electroporation.

Transformation of appropriate host cells with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730–37 (1984); Graham et al., *Virol.*, 52:456 (1973); and Wigler et al., *Proc. Natl. Acad. Sci. USA*, 76:1373–76 (1979).

J. Assays for Recombinant Vectors

Successfully transformed cells, i.e., cells that contain a recombinant DNA molecule of the present invention, can be identified by well known techniques.

For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., Biotech., 3:208 (1985).

In addition to directly assaying for the presence of rDNA, successful transformation can be confirmed by well known immunological methods when the rDNA is capable of directing the expression of a subject polypeptide. For example, cells successfully transformed with a subject rDNA containing an expression vector produce a polypeptide displaying a characteristic antigenicity. Samples of a culture containing cells suspected of being transformed are harvested and assayed for a subject polypeptide using antibodies specific for that polypeptide antigen, such as those produced by an appropriate hybridoma.

Thus, in addition to the transformed host cells themselves, the present invention also contemplates a culture of those cells, preferably a monoclonal (clonally homogeneous) culture, or a culture derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

The present method entails a culture comprising a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture.

Methods for recovering an expressed polypeptide from a culture are well known in the art and include fractionation of the polypeptide-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoabsorption and the like can be performed using well known methods.

A preferred embodiment of the present invention will employ the Lac Z' blue/white phenotype of *E. coli* to allow a visual assay for effective cloning. To use this assay method restriction sites are engineered in-phase with the Lac Z' reading frame. Thus, a DNA fragment inserted into this indicator gene disrupts normal translation of the β-galactosidase protein resulting in white colony phenotypes on growth media containing the chromogenic dye XGAL.

Preferred embodiments of the present invention contain antibiotic resistance genes such as ampicillin resistance gene or kanamycin resistance genes. While these particular kanamycin resistance genes are preferred, other equivalent genes and plasmid such as the genes in the kanamycin resistance Gene Block sold by Pharmacia, or the kanamycin resistance plasmid pMON 530, and the like will be useful.

K. Compositions and Kits

Many of the compounds and groups involved in the instant specification (e.g., nucleic acids) have a number of forms, particularly variably protonated forms, in equilibrium with each other. As the skilled practitioner will understand, representation herein of one form of a compound or group is intended to include all forms thereof that are in equilibrium with each other.

In the present specification, "uM" means micromolar, "ul" means microliter, and "ug" means microgram.

The compositions serving as host vectors can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of polynucleotide primer(s), plasmids, restriction enzyme(s), DNA polymerase, DNA ligase, or a combination thereof. An aliquot of each component sufficient to perform at least one program of cloning will be provided in each container.

In preferred embodiments, the vector is operatively linked to a label, e.g., indicator gene, thereby providing a means to detect a DNA segment incorporated into a target plasmid. Preferred labels are well known to those skilled in the art and include those discussed hereinbefore, especially the Lac Z' visual marker. Other selectable markers may be used and are well known in the art.

Kits useful for producing a template-complement or for amplification or detection of a specific nucleic acid sequence using a primer extension reaction methodology also typically include, in separate containers within the kit, dNTPs where N is adenine, thymine, guanine and cytosine, and other like agents for performing primer extension reactions.

The reagent species, indicating means or primer extension reaction reagents of any system described herein can be provided in solution, as a liquid dispersion or as a substantially dry powder, e.g., the plasmids may be provided in lyophilized form. Where the reagent species or indicating means is an enzyme, the enzyme's substrate can also be provided in a separate package of a system. A solid support and one or more buffers can also be included as separately packaged elements in this system.

The present invention is more fully understood by the specific examples described hereinbelow, and by the appended claims.

EXAMPLES

1. Preparation of Modified Plasmids

The starting plasmids selected for vector construction were of the pT7T319U variety (Mead et al., Protein Engineering, 1:67–74 (1986)), which is a derivative of pTZ19U and is available from Pharmacia LKB.

Complementary single strands of nucleic acids were synthesized with an automatic DNA synthesizer, Pharmacia "Gene Assembler", using the manufacturer's recommended conditions. The single stranded sequences were allowed to hybridize thereby giving a complementary asymmetric DNA duplex having the nucleotide sequence shown in FIG. 1. This oligonucleotide allows digestion by Xcm I at two sites (between residues 18 and 19 on the upper chain and between residues 14 and 15 on the lower chain) to form a single, overhanging dTMP terminus on the 3' end of each strand.

The pT7T319U plasmids and oligonucleotides prepared above were separately treated with Hind III and Eco R1 restriction enzymes using reaction conditions recommended by the enzyme supplier, New England Biolabs. The restriction sites involving pT7T319U were selected so that the Lac Z' reading frame of the plasmids would be interrupted by any insert provided therein, thereby allowing a visual assay according to the well known blue/white phenotype of B-galactosidase.

The linearized plasmids were separated from from the small fragments released between the Eco RI and Hind III sites by electrophoresis on a 1% agarose gel and the linearized plasmids were removed from the gel by electroelution. Similarly, the central sequence of the oligonucleotide was separated from its flanking segments released by Eco RI and Hind III.

The purified linearized plasmids and oligonucleotides were admixed in the ratio of 1:1 to 1:3, and ligated with T4 DNA ligase (New England Biolabs, Beverly, Mass.) under reaction conditions described by the supplier. The recombinant plasmids so formed are designated pTA12 herein. FIG. 1A depicts the gene maps of the host and pTA12 plasmids.

Preparation of Cloning Vector pTA12 plasmids prepared as in Example 1 were digested with Xcm 1 according to procedures recommended by the supplier, New England Biolabs. The small fragment between the two Xcm 1 restriction sites (see FIG. 1B) was separated from the large host fragment by electrophoresis on a 1% agarose gel followed by electroelution, or, in some cases, by differential precipitation with isopropanal.

The isolated linearized pTA12, designated pTA12-L, was ligated separately with each of the following unpurified PCR amplification products: (1) ribosomal RNA genes amplified from genomic DNA of *Sarcophaga bullata*, (2) ribosomal RNA genes amplified from genomic DNA of *Vairimorpha necatrix*, and (3) myosin heavy chain gene amplified from genomic DNA of *Caenorhabditis elegans*.

The primers used in generating the PCR amplified nucleic acids were the following:

C. elegans
CCTGGGCGACGAACCAGTAA
CGCCACCAAGGGAGACCAGG
S. Bullata
CTGGTTGATCCTGCCAG
GGTTACCTTGTTACGACTT
V. necatrix
GGAGGAAAAGAAACTAAC
TTGGAGACCTGCTGCGG The ligation reactions were performed using T4 DNA ligase under the following conditions:

25 mM Tris-HCl (pH 7.8) 10 mM MgCl$_2$ 1 mM DTT 1 mM ATP

50–100 ng vector DNA (gel purified Xcm I digested pTA 12)

1–9 µl PCR reaction products (unpurified)

1 µl T4 DNA ligase (New England Biolabs)

Each reaction admixture was maintained at 16° C. for 16–24 hours. The reaction products formed were used to transform cells for assay of cloning efficiency as described hereinbelow with the results presented in Table 1.

TABLE 1

| Vector End | | Colony Phenotype | | % white | Colonies with |
|---|---|---|---|---|---|
| (plasmid + enzyme) | Insert | Blue | White | total | inserts |
| T-extended (50 ng pTA12/Xcm I) | none (self-ligated) | 2660 | 30 | 1.1% | ND |
| T-extended (50 ng pTA12/Xcm I) | PCR (10 ng S.bullata) | 368 | 65 | 15.0% | 23/24 |
| T-extended (50 ng pTA12/Xcm I) | PCR (10 ng V. necatrix) | 256 | 27 | 9.5% | 23/24 |
| T-extended | PCR | 608 | 78 | 11.4% | 8/10 |

TABLE 1-continued

| Vector End (plasmid + enzyme) | Insert | Colony Phenotype Blue | Colony Phenotype White | % white total | Colonies with inserts |
|---|---|---|---|---|---|
| (50 ng pTA12/Xcm I) T-extended | (10 ng C.elegans) blunt | 4100 | 60 | 1.4% | 3/6 |
| (50 ng pTA12/Xcm I) blunt | (125 ng M13 mp 18/Alu I) none | 3000 | 40 | 1.1% | ND |
| (150 ng pTZ18U/Sma I) blunt | (self-ligated) PCR | 4140 | 120 | 2.8% | 0/22 |
| (150 ng pTZ18U/Sma I) blunt | (10 ng S.bullata) PCR | 15520 | 3920 | 20.2% | 7/96 |
| (50 ng pTZ18U/Sma I) blunt | (10 ng C.elegans) blunt | 2120 | 4530 | 68% | ND |
| (150 ng pTZ18U/Sma I) | (125 ng M13 mp 18/Alu I) | | | | |

3. Transformation and Assay of Xcm 1 Generated Vectors

Approximately 10 μL of each ligation admixture prepared in Example 2 was individually used to transform a competent DH1αF strain of E. coli. The transformed cells were then plated on media containing XGAL.

The number of blue and white colonies were recorded and selected white colonies were analyzed for inserted DNA fragments by purifying small amounts of the plasmid DNA and restricting with the appropriate restriction enzyme. The results are presented in Table 1. A total of 120 white colonies were assayed for inserts and 108 (90%) contained fragments corresponding to the original PCR products.

The ratio of white colonies to blue colonies obtained from the above experiments range from 0.01 to 0.15. The calculated cloning efficiencies were approximately 1–5 –10$^4$ colonies/μg of PCR product. Optimal cloning efficiencies of approximately 12% white/total number of colonies using competent cells able to yield 10$^8$ cells/μg of supercoiled DNA were obtained.

The results presented in Table 1 afford several important observations. First, the ligation results for blunt-ended pTZ18U restricted with Sma I and blunt-ended M13mp18 restricted with Alu I indicate that the chosen ligation conditions are favorable for ligation. Second, a comparison of the cloning efficiencies of S. bullata and C. elegans PCR products with Xcm1 digested pTA12 (T-extended) plasmids with the efficiencies of cloning to Sma 1 digested pTZ18U (blunt) plasmids reveals a much higher cloning efficiency with the T-extended plasmids. Third, the X-cm 1 digested pTA12 plasmids even show good cloning efficiencies with blunt-ended fragments, e.g., M13mp18/Alu 1.

4. Assay of Hph 1 Generated Vectors

Recombinant vectors including two Hph 1 restriction sites were prepared using similar techniques to those for construction of the Xcm 1 vectors described above.

Briefly, PTA112 was derived from the PHSS6 (FIG. 2A) described by in Proc. Natl. Acad. Sci., U.S.A., 83:735–739 (1986) in the following manner. The pH 556 plasmid was digested with the restriction endonuclease Not I. The resulting fragment containing the kanamycin resistance gene and the origin of replication was isolated.

Figure 2A:
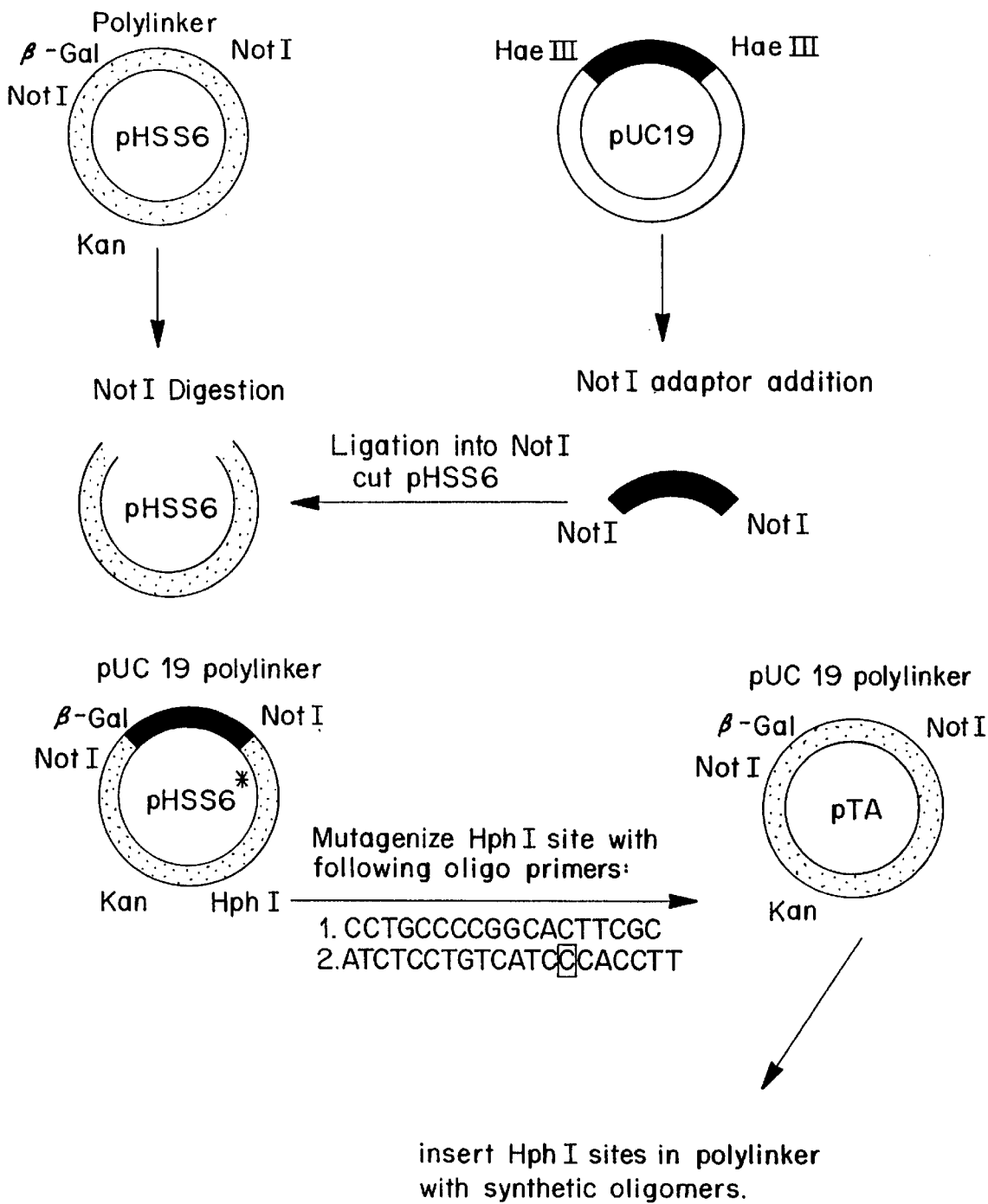
FIG. 2A presents a diagram showing the construction of a vector containing 2 Hph I sites. The vector is kanamycin resistant and has a color indicator system (β galactosidase).

A Hae III fragment containing the PUC 19 polylinker region and the β galactosrdase gene was isolated from PUC 19 by restriction digestion with Hae III. Not I linkers (New England Biolabs) were ligated to the Hae III fragment. After removing the extra Not I linkers by restriction endonuclease digestion this β galactosidase containing fragment was ligated inserted to the kanamycin resistance gene containing fragment isolated above to produce pH SS6* (FIG. 2A).

pH SS6* was mutagenized using the oligo primers and the standard polymerase chain reaction mutagenisis procedure described in *PCR Protocols*, Academic Press, New York (1990) to remove the Hph I site present in the kanamycin resistance gene. This mutagenisis procedure produced pTA (FIG. 2A).

Figure 2B:
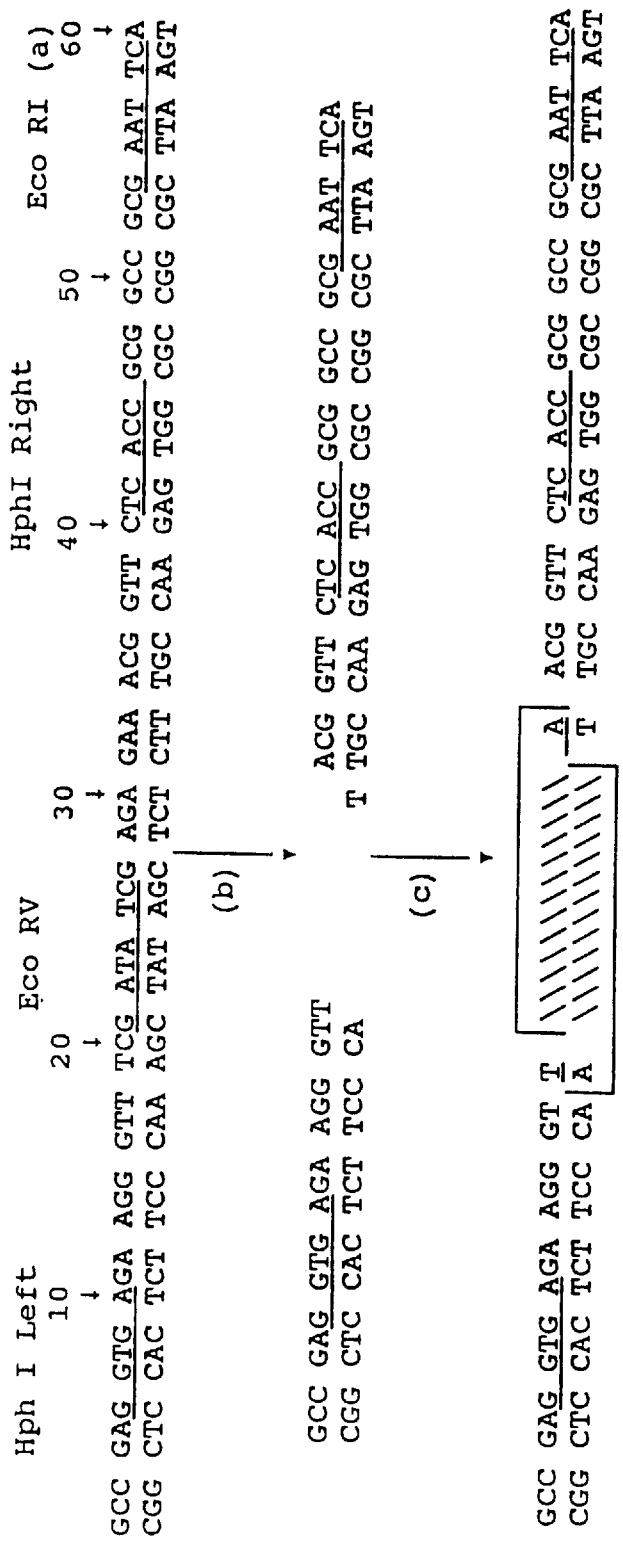
FIG. 2B presents a representative DNA sequence of plasmids constructed to include an Hph I restriction site on either side of an Eco RV recognition site. One Hph I site is present in the host vector while the second Hph I site is provided by an inserted oligonucleotide. Also, the result of Hph I digestion is depicted as well as the result of ligation with terminal 3'-dAMP nucleic acids.

The polylinker of the PTA was replaced with the Hph I-containing polylinker shown in FIG. 2B by digesting pTA with Eco RI and Eco RV restriction endonucleases and ligating the Hph I-containing polylinker to it to produce pTA 112. pTA 112 was linearized with HpH I and the resulting large fragment purified and designated pTA 112-L.

The cDNA fragments were generated by PCR amplification of MS2 RNA, supplied by Boehringer Mannheim (Mannheim, West Germany). cDNA templates of the RNA were prepared following the procedure described by G ulder, U. et al., *Gene*, 25:263 (1983).

The cDNA precursors were amplified via PCR using forward and reverse primers corresponding to the terminal sequences of the cDNA fragments. The primers were synthesized on a Pharmacia "Gene Assembler". The forward primer had the sequence 5'-CCTTAGGTTCTGGTAATGAC-3' and the reverse primer had the sequence 5'-GGGTGCAATCTCACTGGGAC- 3'.

PCR amplification conditions followed those recommended by the manufacturer and were:
 100 ng plasmid (900 bp MS2)
 0.2 μg primer (forward/reverse)
 1 μL 25mM dNTP's
 5 μL 10×PCR buffer
 50 μL total volume
Cycles: (1) 94° C., 1 min; 55° C., 2 min; 72° C., 3 min
 (2) 72° C., 7 min;
 (3) 25° C., 10 min.

The fragments were amplified by PCR using three different polymerases: (1) "Taq" polymerase, isolated from *Thermus aquaticus* and obtained from Perkin Elmer Cetus, (2) "Vent" polymerase, purchased from New England Biolabs, and (3) the thermophilic polymerase, "Thermo", isolated from *Thermus flavus*, and obtained from Molecular Biology Resources. These unpurified PCR products were ligated with an Hph 1 analog of pTA12, hereinbelow called pTA112, using procedures described above for Xcm 1 recognized plasmids. The nucleotide sequence for the synthetically prepared oligonucleotide having Eco RI and Eco RV termini is shown in FIG. 2, as is the result of Hph 1 digestion and ligation with 3'-dAMP PCR products.

The results presented in Table 2 allow comparisons of cloning efficiencies for Hph 1 digested (T-extended) pTA112 plasmids and blunt-ended control plasmids (pTA112 digested with Eco RV) using unpurified PCR amplified MS2 which was generated with three different polymerases.

Thus, Hph 1 digested plasmids show near 100% cloning efficiencies with each polymerase studied and over a 3-fold range in PCR product ratio. Most significantly, the reactions of T-extended (Hph 1 digested) plasmids and of blunt-ended (Eco RV digested) plasmids of Taq-generated MS2 products indicate that the d-AMP terminal MS2 products are more than ten times more efficiently cloned into the T-extended plasmids than the blunt-ended vectors.

5. Representative Kit

A representative kit for use in directly cloning DNA segments having terminal 3'-dAMP residues includes one or more, and preferably all, of the following components in separate containers:

| Component Designation | Description |
|---|---|
| | Box 1: |
| TA1 | Sterile water: 1 mL |
| TA2 | 10 × ligation buffer: 100 μL |
| TA3 | Ligation-ready cloning vector: 1.1 μg (lyophilized pTA112-L or pTA12-L) |
| TA4 | 1 × Tris EDTA buffer: 100 μL |
| TA5 | T4 DNA ligase: 22 μL |
| TA6 | Control vector: 1 μg/10 μL Tris EDTA |
| TA7 | Forward primer: (0.2 μg/μL): 5 μL |
| TA8 | Reverse primer: (0.2 μg/μL): 5 μL |
| TA9 | 10 × PCR buffer: 100 μL |
| TA10 | 25 mM dNTPs (deoxynucleoside triphosphates) |
| TA11 | 0.5 M BME |
| TA12 | Supercoiled plasmid pUC18 (control): 10 μL |
| | Box 2: |
| TA13 | 21 aliquots of competent E. coli cells (strain JM109 or NM522 are preferred) at 50 μL |
| TA14 | SOC Medium for culturing said cells about 20 ml (p A.2 of Molecular Cloning: A Laboratory Manual, Second Edition, Sanbrook, et al., Cold Spring Harbor Press (1989)) |

The above kit will provide sufficient reagents for performing 20 cloning reactions.

In one preferred embodiment, the kit includes at least components TA3, TA6, TA7, and TA8.

In another preferred embodiment, the kit includes at least components TA3, TA4, TA6, TA7, TA8, TA13, and TA14.

In a further preferred embodiment, the kit includes at least components TA3 and TA13.

Although the present invention has been described in some detail by way of illustration and example for purposes of clarity and understanding, it will be obvious that certain modifications may be practiced within the scope of the appended claims. Therefore, the scope of the invention, and equivalents thereof, should be determined with reference to the appended claims rather than with reference to the above description.

TABLE 2

| Vector End (plasmid + enzyme) | Insert | Colony Phenotype | | % white total | Colonies with inserts(%) |
|---|---|---|---|---|---|
| | | Blue | White | | |
| T-extended (50 ng pTA112/Hph I) | none | 73 | 3 | 3.9% | N/D |
| T-extended (50 ng pTA112/Hph I) | Taq-PCR (16 ng MS2) | 78 | 13 | 14.3% | >95 |
| T-extended (50 ng pTA112/Hph I) | Vent-PCR (16 ng MS2) | 85 | 17 | 16.7% | >95 |
| T-extended (50 ng pTA112/Hph I) | Thermo-PCR (16 ng MS2) | 113 | 18 | 13.7% | >95 |
| T-extended (50 ng pTA112/Hph I) | Taq-PCR (48 ng MS2) | 84 | 20 | 19.2% | >95 |
| T-extended (50 ng pTA112/Hph I) | Vent-PCR (48 ng MS2) | 89 | 20 | 19.5% | >95 |
| T-extended (50 ng pTA112/Hph I) | Thermo-PCR (48 ng MS2) | 71 | 18 | 18.2% | >95 |
| blunt-ended (50 ng pTA112/Eco RV) | none | 1500 | 15 | 1.0% | N/D |
| blunt-ended (50 ng pTA112/Eco RV) | Taq-PCR (16 ng MS2) | 2000 | 42 | 1.2% | N/D |
| blunt-ended (50 ng pTA112/Eco RV) | Taq-PCR (48 ng MS2) | 2000 | 50 | 2.4% | N/D |

What is claimed is:

1. A kit for direct cloning of PCR amplified nucleic acids comprising, in separate containers, an aliquot of linear plasmid DNA molecules comprising a single overhanging 3'-dTMP termini; and an aliquot of a DNA ligase, said DNA ligase capable of ligating a nucleic acid sequence comprising a 3'-dAMP overhang into said linear plasmid DNA at said overhanging 3' dTMP sites.

2. The kit of claim 1 which further comprises, in a separate container, an aliquot of control plasmids.

3. The kit of claim 1 which further comprises, in a separate container, an aliquot of competent host cells capable of replicating said plasmids upon transformation with said plasmids.

4. The kit of claim 1 wherein said linear plasmids are lyophilized.

5. The kit of claim 1 which further comprises, in a separate container, an aliquot of primer molecules for PCR amplification of a target DNA.

6. The kit of claim 1 which further comprises, in a separate container, an aliquot of each of forward and reverse PCR primers suitable for PCR amplification of said nucleic acid.

* * * * *

UNITED STATES PATENT AND TRADEMARK OFFICE
CERTIFICATE OF CORRECTION

PATENT NO. : 5,827,657
DATED : October 27, 1998
INVENTOR(S) : Corinna Herrnstadt, et al.

It is certified that error appears in the above-identified patent and that said Letters Patent is hereby corrected as shown below:

Column 1, line 67: "tG" should read --to--
Column 2, line 36: "of 5" should read --of--
Column 2, line 39: "3 '-dAMP" should read --3'-dAMP--
Column 2, line 43: "Thus..." should not begin a new paragraph
Column 4, line 59: "Analoa" should read --Analog--
Column 5, line 22: "mole[|ule" should read --molecule--
Column 7, line 16: "Including" should read --including--
Column 9, line 60: "Particularly..." should not begin a new paragraph
Column 9, line 67: "40-terminal" should read --3'terminal--
Column 11, line 46: " $^{32}$p" should read -- $^{32}$P--
Column 13, line 36: "termini-complementary" should read --termini.complementary--
Column 14, line 44: "Fragment" should read --fragment--
Column 15, line 4: "Tag" should read --Taq--
Column 15, line 47: "For example..." should not begin a new paragraph
Column 19, line 35: "-10 $^{4}$" should read --x 10 $^{4}$--

Signed and Sealed this

Fifteenth Day of February, 2000

Attest:

Q. TODD DICKINSON

Attesting Officer

Commissioner of Patents and Trademarks